United States Patent [19]

Davenport et al.

[11] Patent Number: 4,560,789

[45] Date of Patent: Dec. 24, 1985

[54] PROCESS FOR PRODUCING 4-ACETOXYACETANILIDE

[75] Inventors: Kenneth G. Davenport; Charles B. Hilton, both of Corpus Christi, Tex.

[73] Assignee: Celanese Corporation, New York, N.Y.

[21] Appl. No.: 627,381

[22] Filed: Jul. 3, 1984

[51] Int. Cl.[4] ................... C07C 103/46; C07C 103/38
[52] U.S. Cl. ...................................... 560/142; 564/223
[58] Field of Search ........................ 560/142; 564/223

[56] References Cited

U.S. PATENT DOCUMENTS 2,833,825  5/1978  Lewis ................................. 568/310
4,347,372  8/1982  Föry et al. ........................ 560/142
4,524,217  6/1985  Davenport et al. ............... 564/223

FOREIGN PATENT DOCUMENTS 2616986  10/1977  Fed. Rep. of Germany .

OTHER PUBLICATIONS

Auwers et al, Chemishe Berichte, 58, 36–51, (Germany 1925).
Ganboa et al, Synthetic Communications, 13 (11), 941–944, (1983).
Pearson et al, J. Amer. Chem. Soc., 75, 5905–5908, (1953).
Simons et al, J. Amer. Chem. Soc., 62, 485 and 486, (1940); 61, 1795 and 1796 (1939).
Dann and Mylius, Annalen der Chemie, 587 Band, 1–15, (W. Germany, 1954).

*J. Pharmaceutical Sciences*, vol. 59, No. 12, pp. 1738–1741; Rattie et al.
Fieser and Fieser, *Organic Chemistry*, 3rd Ed., Reinhold Publ. Corp., New York, 1956, pp. 211–212, 627.

*Primary Examiner*—Natalie Trousof
*Assistant Examiner*—Patricia M. Scott
*Attorney, Agent, or Firm*—M. Turken; D. R. Cassady

[57] ABSTRACT

4-Acetoxyacetanilide is produced by subjecting phenyl acetate to a Fries rearrangement or phenol and an acetylating agent to a Friedel-Crafts acetylation to form 4-hydroxyacetophenone which is then reacted with hydroxylamine or a hydroxylamine salt to form 4-hydroxyacetophenone oxime. The oxime is then subjected to a Beckmann rearrangement and accompanying acetylation with acetic anhydride to form the 4-acetoxyacetanilide.

7 Claims, No Drawings

PROCESS FOR PRODUCING 4-ACETOXYACETANILIDE

This invention relates to an integrated process for the production of 4-acetoxyacetanilide (AAA) from phenyl acetate, or phenol and acetic acid as the starting material.

BACKGROUND OF THE INVENTION

It is known to produce 4-acetoxyacetanilide by preparing the sodium salt of N-acetyl-para-aminophenol (APAP) and reacting such sodium salt with acetic anhydride. The APAP used as the starting material for the foregoing reaction is in turn prepared by catalytic hydrogenation of nitrobenzene with concomitant rearrangement in the presence of a platinum catalyst and aqueous sulfuric acid to form para-aminophenol, and acetylation of the latter compound with acetic anhydride to form the N-acetyl-para-aminophenol. This process is believed to present certain problems however, such as recovery of dissolved platinum catalyst used in the nitrobenzene reduction step. Furthermore, the acetylation step may present problems, such as the difficulty of monoacetylating the hydroxy aromatic amine, oligomerization of the hydroxy aromatic amine and color body formation.

It is also known to prepare APAP by hydrogenating 4-nitro-chlorobenzene to a 4-chloroaniline which is then reacted with aqueous KOH to form para-aminophenol. This is then acetylated as described previously to form the N-acetyl-para-aminophenol. This process is relatively complex requiring a fair number of reaction and purification steps. Moreover, the acetylation step in this process is believed to give rise to the same problems as occurs in the acetylation step of the nitrobenzene process described previously.

The preparation of hydroxy aromatic ketones by the Fries rearrangment of aromatic esters is well-known in the art. Thus, Lewis, U.S. Pat. No. 2,833,825 shows the rearrangement of phenyl or other aromatic esters to acylphenols or other hydroxy aromatic ketones using anhydrous hydrogen fluoride as catalyst. The examples of this patent are limited to the rearrangement of esters of higher fatty acids with the yields ranging from 55 to 95%.

Simons et al, Journal of the American Chemical Society, 62, 485 and 486 (1940) show the use of hydrogen fluoride as a condensing agent for various rearrangements and at page 486 show the Fries rearrangement of phenyl acetate to obtain p-hydroxyacetophenone.

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15 (1954), show the rearrangement of phenyl acetate in hydrogen fluoride to 4-hydroxyacetophenone, with a maximum yield of 81% after 24 hours of reaction time, and report a yield of 92% stated to be obtained by K. Weichert as reported in Angewandte Chemie 56, 338 (1943). However, Dann and Mylius suggest that the difference in yields may be at least partly due to the previous ignoring by Weichert of the accompanying 2-hydroxyacetophenone.

Dann and Mylius also disclose the reaction of phenol and glacial acetic acid in the presence of hydrogen fluoride to produce 4-hydroxyacetophenone at a yield of 61.6%. This reaction may be conventionally characterized as a Friedel-Crafts acetylation of phenol with acetic acid as the acetylating agent.

Simons et al, Journal of the American Chemical Society, 61, 1795 and 1796 (1939) teach the acylation of aromatic compounds using hydrogen fluoride as a condensing agent and in Table 1 on page 1796 show the acetylation of phenol with acetic acid to produce p-hydroxyacetophenone in 40% yield.

Meussdoerffer et al, German Offenlegungsschrift 26 16 986 published Oct. 27, 1977 and assigned to Bayer AG, disclose the acylation of phenolic compounds such as phenol itself with an acyl halide such as acetyl chloride to form hydroxy aromatic ketones.

Auwers et al, Chemische Berichte 1925, 58, 36-51, at page 41 show the Beckmann rearrangement of a large number of oximes of aromatic ketones most of which are substituted acetophenones. However, the only attempted rearrangement of the oxime of a ring-unsubstituted hydroxy aromatic ketone was that of the oxime of o-hydroxyacetophenone, but no amine was formed, i.e. the attempted rearrangement was unsuccessful; see Auwers et al at page 41.

Ganboa et al, Synthetic Communications 13(11), 941-944 (1983) show the production of acetanilide from acetophenone by refluxing in a solution of hydroxylamine hydrochloride. There is however no suggestion of the synthesis of N-acyl acyloxy aromatic amines such as 4-acetoxyacetanilide.

Pearson et al, Journal of the American Chemical Society 75 5905-5908 (Dec. 5, 1953) disclose the formation of hydrazones from ketones by reaction with hydrazine hydrate and the rearrangement of the hydrazone to the amide by reaction with sodium nitrite and concentrated sulfuric acid. Specifically, on page 5907 Pearson et al show the rearrangement of p-hydroxyacetophenone hydrazone to p-hydroxyacetanilide, i.e. APAP.

SUMMARY OF THE INVENTION

In accordance with this invention, 4-acetoxyacetanilide (AAA) is produced from phenyl acetate, or phenol and an acetylating agent such as acetic acid, by means of an integrated process including the steps of converting the phenyl acetate, or phenol and an acetylating agent, to 4-hydroxyacetophenone by a Fries rearrangement or Friedel-Crafts acetylation respectively, and converting the 4-hydroxyacetophenone to the corresponding ketoxime with hydroxylamine or a hydroxylamine salt. The ketoxime is then subjected to a Beckmann rearrangement and accompanying acetylation by contacting the ketoxime with acetic anhydride and a Beckmann rearrangement catalyst to form the 4-acetoxyacetanilide.

Although the reaction of phenol and an acetylating agent is characterized herein as a "Friedel-Crafts acetylation," no opinion as to the mechanism of reaction should be implied by this characterization.

When carrying out the process of this invention using phenyl acetate as the starting material, the initial Fries rearrangement to produce 4-hydroxyacetophenone (4-HAP) from phenyl acetate is defined by equation (I):

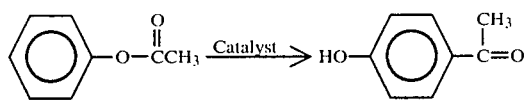

(I)

If phenol and an acetylating agent are used as the starting material, the resulting acetylation reaction to form 4-HAP is indicated by equation (II):

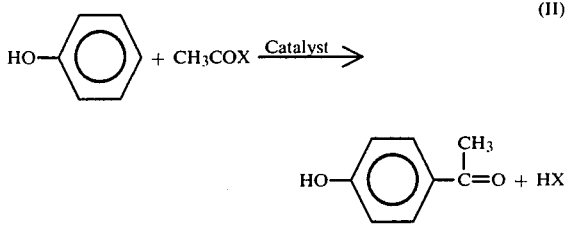

(II)

where X is the residue minus an acetyl group of compounds which are known acetylating agents. X may be, for example, hydroxy, acetoxy, or halide including fluoride, chloride, bromide, or iodide. Acetylating agents which may be used are for example, acetic acid, acetic anhydride, acetyl flouride, acetyl chloride and acetyl bromide.

The formation of the ketoxime of 4-HAP, i.e. 4-HAP oxime, proceeds as in equation (III):

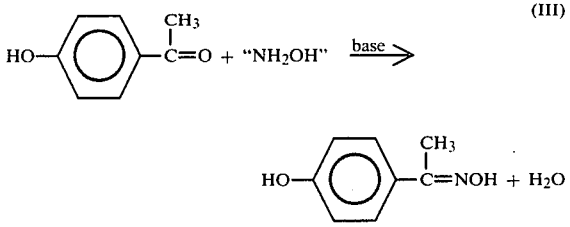

(III)

The Beckmann rearrangement and accompanying acetylation of the 4-HAP oxime to produce AAA proceeds as in equation (IV):

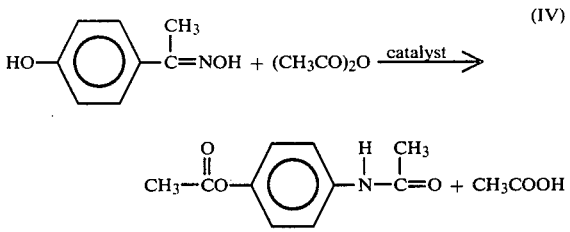

(IV)

The Fries rearrangement or Friedel-Crafts catalyst may be hydrogen fluoride or any other catalyst known in the art to be effective for the Fries or Friedel-Crafts reaction, e.g. aluminum chloride, zinc chloride, or boron trifluoride. In carrying out the reaction, the phenyl acetate, or phenol and acetylating agent, catalyst, and if desired when phenyl acetate is the starting material, an additive for the reaction such as acetic anhydride or acetic acid, may be charged to a corrosion-resistant reactor and the mixture maintained at a temperature, for example, of about 20° to about 100° C. for a period, for example, of about ½ to about 4 hours, at a pressure, for example, of about 50 to about 500 psia. If HF is used as the catalyst it may be charged as a liquid or a gas using technologies of handling well-known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 75 moles per mole of phenyl acetate or phenol initially present in the reaction zone.

The conversion of 4-hydroxyacetophenone (4-HAP) into 4-acetoxyacetanilide (AAA) is accomplished by first forming the ketoxime from the 4-HAP as indicated by equation (III), by contacting the 4-HAP with hydroxylamine or a salt of hydroxylamine, e.g. hydroxylamine hydrochloride, hydroxylamine sulfate, hydroxylamine bisulfate, or hydroxylamine phosphate and a base, such as ammonium hydroxide, potassium hydroxide, sodium hydroxide, or lithium hydroxide in an amount, for example, of 1 to 3 moles per mole of hydroxylamine, at a temperature, for example of 0° to 60° C. for a period, for example, of 1 to 4 hours. Any pressure may be used, e.g. 80 mm. of mercury to 10 atmospheres absolute. The reaction is preferably carried out in an aqueous or alcoholic medium, i.e. in the presence of water and/or an alcohol such as methanol, ethanol or isopropanol.

The 4-HAP oxime is converted into AAA by a Beckmann rearrangement and accompanying acetylation as shown in equation (IV), by contacting the oxime with acetic anhydride and a Beckmann rearrangement catalyst at a temperature, for example of 0° to 118° C. for a period for example of 1 to 4 hours. The pressure is not critical and may be, for example, in the range of 80 mm. of mercury to 10 atmospheres absolute. Any Beckmann rearrangement catalyst may be used as, for example, an acid, e.g. a mineral acid such as sulfuric or hydrochloric acid, an organic acid such as trifluoroacetic acid, para-toluenesulfonic acid, benzenesulfonic acid, or methanesulfonic acid, or an acidic ion-exchange resin such as Amberlyst 15 or Nafion 501 which are sulfonic acid ion-exchange resins, or thionyl chloride in liquid sulfur dioxide. The reaction may be advantageously carried out in the presence of glacial acetic acid in an amount, for example, up to 50% by weight of the acetic anhydride. The total amount of glacial acetic acid is not critical but the total amount of anhydride or anhydride/acid mixture is such that the oxime concentration in most cases is in the range of about 2% to 50% weight at the start of the reaction.

The following examples further illustrate the invention.

EXAMPLE 1

This example illustrates the preparation of 4-hydroxyacetophenone by the Fries rearrangement of phenyl acetate using hydrogen fluoride as catalyst.

To a 300 cc Hastelloy C autoclave was charged 40.8 g (0.3 mol) of phenyl acetate. The autoclave was sealed, immersed in a dry ice/isopropanol bath and cooled internally to −45° C., and evacuated to ca. 100 Torr. Addition of 120 g (6.0 mol) of anhydrous hydrogen fluoride was performed in a manner such as that the internal temperature of the autoclave did not exceed 0° C. The internal pressure of the reactor was then adjusted to 0 psig with nitrogen. The contents of the autoclave were stirred and heated to 75° C. for 1 h. The hydrogen fluoride was vented over a 45 min period at ca. 45° C. The mixture was poured onto 25 g of ice and neutralized with 45% potassium hydroxide solution. The aqueous mixture was extracted with ethyl acetate. The organic fraction was then dried over anhydrous magnesium sulfate, filtered, and the solvent was removed on a rotary evaporator to yield 44.0 g of a dark green solid corresponding to 99.9% conversion of phenyl acetate and 94.3% selectivity to 4-hydroxyacetophenone.

EXAMPLE 2

This example illustrates the preparation of 4-hydroxyacetophenone by the Fries rearrangement of phenyl acetate using hydrogen fluoride as catalyst with acetic anhydride as additive.

To a 300 cc Hastelloy C autoclave were added 30.6 grams (0.3 mole) of acetic anhydride. The autoclave was cooled to $-50°$ C. and evacuated to 5 Torr whereupon 120 g (6.0 mole) of anhydrous hydrogen fluoride was transferred from a cylinder to the autoclave. After the transfer of hydrogen fluoride was completed, the internal temperature and the internal pressure of the autoclave was adjusted to $-50°$ C. and 0 psig using nitrogen, respectively. To the stirred autoclave was added 81.6 g (0.6 mol) of phenyl acetate at such a rate that the temperature of the mixture did not exceed $-23°$ C. Upon completion of phenyl acetate addition, the contents were warmed to 50° C. and stirred for 3 h during which time a pressure of ca. 40 psig was generated. At the end of the run, the hydrogen fluoride was vented through a caustic scrubber and the contents of the autoclave were poured onto ca. 30 g of ice. The pH of the mixture was adjusted to 6.5 using 45% potassium hydroxide and the mixture was then extracted with 75 ml of ethyl acetate (3x). The organic solution was dried over anhydrous magnesium sulfate, filtered, and the solvent was removed using a rotary evaporator.

The reaction resulted in 98.1% conversion of phenyl acetate with the following selectivities: phenol 1%; 4-hydroxyacetophenone (4-HAP) 82.3%; 2-hydroxyacetophenone (2-HAP) 4.3%; 3-hydroxyacetophenone (3-HAP) 0.1%; 4-acetoxyacetophenone (4-AAP) 3.8%; and 4-(4'-hydroxyphenyl)-acetophenone (HPAP) 0.4%.

EXAMPLE 3

This example describes the formation of 4-hydroxyacetophenone by the Fries rearrangement of phenyl acetate using hydrogen fluoride as catalyst and acetic acid as additive.

The procedure for Example 2 was repeated except that 18 grams (0.3 mole) of acetic acid rather than acetic anhydride were charged to the reactor before it was cooled and charged with the hydrogen fluoride. A conversion of 99.0% of phenyl acetate was obtained with the following selectivities: phenol 3.3%; acetic acid 0.8%; 4-HAP 80.8%; 3-HAP 0; 2-HAP 5.8%; 4-AAP 0.3% and HPAP 0.3%.

EXAMPLE 4

This example illustrates the preparation of 4-hydroxyacetophenone (4-HAP) by the Friedel-Crafts acetylation of phenol with acetic acid as the acetylating agent.

Phenol (9.4 g, 0.1 moles) and acetic acid (12.0 g, 0.2 moles) were charged to a 300 ml Hastelloy C autoclave at room temperature. The reactor was evacuated and cooled to $-20°$ C. HF (100 g, 5 moles) was then transferred into the reactor. The reactor was heated to 80° C. and maintained for 1 hour at reaction temperature. At the end of the reaction the reactor was cooled to 20° C. and the excess HF was vented to a KOH scrubber. Ethyl acetate was added to the contents of the reactor. The mixture was then neutralized with 45% aqueous KOH. The resulting organic phase was separated, dried over $MgSO_4$ and evaporated to afford a yellow solid which contained 13.1 g (0.096 moles) of 4-HAP.

EXAMPLE 5

This example illustrates the formation of 4-hydroxyacetophenone oxime from 4-hydroxyacetophenone and hydroxylamine hydrochloride.

A solution was prepared by adding 13.6 g (0.1 mol) of 4-hydroxyacetophenone, 7.6 g (0.11 mol) of hydroxylamine hydrochloride, and 10 g of water to 40 mL of ethanol. To the solution was added 5.0 g of 30% ammonium hydroxide which was then heated at reflux for 2 h. The ethanol was removed on a rotary evaporator to yield a yellow oil. An extractive work-up afforded 15.1 g (99%) of 4-hydroxyacetophenone oxime.

EXAMPLE 6

This example illustrates the formation of 4-hydroxyacetophenone oxime from 4-hydroxyacetophenone and hydroxylamine sulfate.

A solution was prepared by adding 20.4 g (0.15 mol) of 4-hydroxyacetophenone and 13.0 g (0.08 mol) of hydroxylamine sulfate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 7

This example illustrates the formation of 4-hydroxyacetophenone oxime from 4-hydroxyacetophenone and hydroxylamine phosphate.

A solution was prepared by adding 20.4 g (0.15 mol) of 4-hydroxyacetophenone and 12.9 g (65.6 mmol) of hydroxylamine phosphate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 8

This example illustrates the formation of 4-acetoxyacetanilide (AAA) by the Beckmann rearrangement and accompanying acetylation of 4-hydroxyacetophenone oxime using an acidic ion-exchange resin as catalyst.

A mixture of 3.0 g (22.0 mmol) of 4-hydroxyacetophenone oxime, 3.0 g of Amberlyst 15 (a sulfonic acid ion-exchange resin made by Rohm & Haas), and 75 mL of a mixture of glacial acetic acid and acetic anhydride (1:1) was heated at reflux under nitrogen for 4 h. The ion-exchange resin was then removed and the acetic acid/acetic anhydride was distilled in vacuo to yield yellow-white crystals. The crystals were dissolved in ethyl acetate and treated with activated carbon and anhydrous magnesium sulfate. The mixture was filtered and the solvent was removed on a rotary evaporator to yield 3.4 g (80.4%) of yellow crystals of 4-acetoxyacetanilide (AAA).

EXAMPLE 9

This example illustrates the formation of 4-acetoxyacetanilide (AAA) by the Beckmann rearrangement and accompanying acetylation of 4-hydroxyacetophenone oxime using methanesulfonic acid as catalyst.

A solution of 10 g (66.2 mmol) of 4-hydroxyacetophenone oxime, 1.6 of 70% methanesulfonic acid, 50 g of acetic anhydride and 100 g of glacial acetic acid was heated at reflux under nitrogen for 2 h. Rotary evaporation of the solution yielded 17.0 g of light brown crystals. Recrystallization from water yielded 6.7 g (52.4%) of 4-acetoxyacetanilide (AAA). The mother liquor contained 32.0% of AAA for a total yield of 84.4%.

EXAMPLE 10

This example illustrates the formation of 4-acetoxyacetanilide by the Beckmann rearrangement and accompanying acetylation of 4-hydroxyacetophenone oxime using phosphoric acid ($H_3PO_4$) as catalyst.

To a mixture of 100 g of glacial acetic acid, 50 g of acetic anhydride, and 3.6 g of 85% $H_3PO_4$, sparged with nitrogen for 30 minutes, was added 10 g of 4-hydroxyacetophenone oxime. The mixture was heated at reflux for 1 hour under a nitrogen atmosphere, then cooled to room temperature and neutralized with 13% $Na_2CO_3$. The mixture was evaporated to dryness using a rotary evaporator and the solid was dissolved in 200 g of boiling water. After hot filtration, the solution was allowed to cool and stand overnight. The ensuing white crystals were collected, washed with 20 mL of water, and dried in a vacuum oven (60° C./100 mm Hg) for 2 hours. Upon drying, 9.4 g (73.9%) of white crystalline plates of 4-acetoxyacetanilide having a melting point of 148°–150° C. was obtained. An additional 0.8 g of AAA and 1.5 g of N-acetyl-para-aminophenol (APAP) were reclaimed from the mother liquor.

The 4-acetoxyacetanilide (AAA) of this invention may be utilized as a monomer in the preparation of poly(ester-amide)s capable of forming an anisotropic melt phase and suitable for being formed into shaped articles such as molded articles, fibers, and films, as shown, for example, in U.S. Pat. Nos. 4,330,457; 4,339,375; 4,341,688; 4,351,918; and 4,355,132.

The AAA of this invention may also be hydrolyzed to form N-acetyl-para-aminophenol (APAP) which is one of the most widely used over-the-counter analgesics. The following example illustrates this process:

EXAMPLE 11

A mixture of 5 g (25.9 mmol) of 4-acetoxyacetanilide (AAA), of 70% methanesulfonic acid, and 50 g of water was heated at reflux for 1 hr. Upon cooling, white crystals formed. Analysis (GLC) of the crystals as well as the aqueous solution indicated 90% conversion of the AAA to N-acetyl-para-aminophenol (APAP).

We claim:

1. A process comprising contacting phenyl acetate or phenol and an acetylating agent with a Fries - Friedel-Crafts reaction catalyst to form 4-hydroxyacetophenone, contacting the latter with hydroxylamine or a hydroxylamine salt and a base to form 4-hydroxyacetophenone oxime, and contacting said oxime with a Beckmann rearrangement catalyst and acetic anhydride to form 4-acetoxyacetanilide.

2. The process of claim 1 wherein said 4-acetoxyacetanilide is hydrolyzed to form N-acetyl-para-aminophenol.

3. The process of claim 1 wherein hydrogen fluoride is employed as the Fries - Friedel-Crafts reaction catalyst.

4. The process of claim 1 wherein the Fries rearrangement of phenyl acetate is employed to produce 4-hydroxyacetophenone as the first step in the process.

5. The process of claim 1 wherein the Friedel-Crafts acetylation of phenol with acetic acid is employed to produce 4-hydroxyacetophenone as the first step in the process.

6. The process of claim 1 wherein 4-hydroxyacetophenone is contacted with hydroxylamine phosphate to form the oxime.

7. The process of claim 4 wherein said Beckmann rearrangement catalyst is an acidic ion-exchange resin.

* * * * *